(12) United States Patent
Chen

(10) Patent No.: US 8,211,911 B2
(45) Date of Patent: Jul. 3, 2012

(54) COMPOUNDS AS KINASE INHIBITORS

(76) Inventor: Guoqing Paul Chen, Moorpark, CA (US)

( * ) Notice: Subject to any disclaimer, the term of this patent is extended or adjusted under 35 U.S.C. 154(b) by 416 days.

(21) Appl. No.: 12/540,300

(22) Filed: Aug. 12, 2009

(65) Prior Publication Data
US 2010/0048599 A1    Feb. 25, 2010

Related U.S. Application Data

(60) Provisional application No. 61/089,908, filed on Aug. 19, 2008.

(51) Int. Cl.
*A61K 31/04* (2006.01)
*C07D 215/38* (2006.01)
(52) U.S. Cl. ............... 514/312; 514/266.1; 546/153; 544/287
(58) Field of Classification Search ............ 546/153; 544/287; 514/312, 266.1
See application file for complete search history.

(56) References Cited

OTHER PUBLICATIONS

Batchelor, Cancer Cell, VOl 11(1), pp. 83-95, 2007.*
Hormigo, Cancer Cell, VOl 11(1), pp. 6-8, 2007.*
Baka, Expert Opin THer Tarte6ts, VOl 10(6), pp. 867-876, 2006.*

* cited by examiner

*Primary Examiner* — D M Seaman

(57) ABSTRACT

The present invention relates to compounds of Formula I, processes for their preparation, pharmaceutical compositions containing them as active ingredient, methods for the treatment of disease states associated with angiogenesis, such as cancers associated with protein tyrosine kinases, to their use as medicaments for use in the production of inhibition of tyrosine kinases reducing effects in warm-blooded animals such as humans.

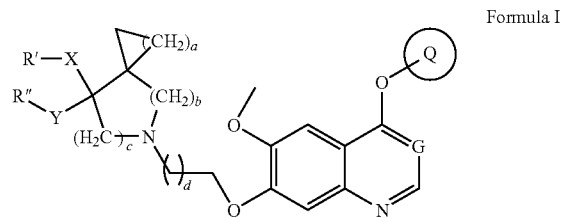

Formula I

9 Claims, No Drawings

COMPOUNDS AS KINASE INHIBITORS

This application claims the benefit of U.S. provisional application: 61/089,908 filed on Aug. 19, 2008.

FIELD OF THE INVENTION

The present invention relates to compounds, processes for their preparation, pharmaceutical compositions containing them as active ingredient, methods for the treatment of disease states associated with angiogenesis, such as cancers associated with protein tyrosine kinases, to their use as medicaments for use in the production of inhibition of tyrosine kinases reducing effects in warm-blooded animals such as humans.

BACKGROUND OF THE INVENTION

Receptor tyrosine kinases are large enzymes that span the cell membrane and possess an extracellular binding domain for growth factors, a transmembrane domain, and an intracellular portion that functions as a kinase to phosphorylate a specific tyrosine residue in proteins and hence to influence cell proliferation. Tyrosine kinases may be classified as growth factor receptor (e. g. EGFR, PDGFR, FGFR and erbB2) or non-receptor (e. g. c-src and bcr-abl) kinases. Such kinases may be aberrantly expressed in common human cancers such as breast cancer, gastrointestinal cancers such as colon, rectal or stomach cancer, leukemia, and ovarian, bronchial or pancreatic cancer. Aberrant erbB2 activity has been implicated in breast, ovarian, non-small cell lung, pancreatic, gastric and colon cancers.

Normal angiogenesis plays an important role in a variety of processes including embryonic development, wound healing and several components of female reproductive function. Undesirable or pathological angiogenesis has been associated with disease states including diabetic retinopathy, psoriasis, cancer, rheumatoid arthritis, atheroma. Tumor angiogenesis, the formation of new blood vessels and their permeability is primarily regulated by (tumor-derived) vascular endothelial growth factor (VEGF), which acts via at least two different receptors: VEGF-R1 (Flt-1); and VEGF-R2 (KDR, Flk-1). The VEGF KDR receptor is highly specific for vascular endothelial cells (Endocr. Rev. 1992, 13, 18; FASEB J. 1999, 13, 9).

A large number of human tumors, especially gliomas and carcinomas, express high levels of VEGF and its receptors. This has led to the hypothesis that the VEGF released by tumor cells stimulates the growth of blood capillaries and the proliferation of tumor endothelium in a paracrine manner and through the improved blood supply, accelerate tumor growth. Direct evidence of the role of VEGF as a tumor angiogenesis factor in vivo is shown in studies in which VEGF expression or VEGF activity was inhibited. This was achieved with anti-VEGF antibodies, with dominant-negative VEGFR-2 mutants which inhibited signal transduction, and with anti-sense-VEGF RNA techniques. All approaches led to a reduction in the growth of glioma cell lines or other tumor cell lines in vivo as a result of inhibited tumor angiogenesis.

Three principal mechanisms play an important part in the activity of angiogenesis inhibitors against tumors: 1) Inhibition of the growth of vessels, especially capillaries, into vascular resting tumors, with the result that there is no net tumor growth owing to the balance that is achieved between cell death and proliferation; 2) Prevention of the migration of tumor cells owing to the absence of blood flow to and from tumors; and 3) Inhibition of endothelial cell proliferation, thus avoiding the paracrine growth-stimulating effect exerted on the surrounding tissue by the endothelial cells which normally line the vessels.

The present invention is based on the discovery of compounds that surprisingly inhibit the effect of VEGF, a property of value in the treatment of disease states associated with angiogenesis and/or increased vascular permeability such cancer, diabetes, psoriasis, rheumatoid arthritis, Kaposi's, haemangioma, acute and chronic nephropathies, atheroma, arterial restenosis, autoimmune disease, acute inflammation, excessive scarformation and adhesions, lymphoedema, endometriosis, dysfunctional uterine bleeding and ocular diseases with retinal vessel proliferation.

It has now been found that compounds of formula I, described below, are a new class of compounds that have advantageous pharmacological properties and inhibit the activity of protein tyrosine kinases, such as VEGFr, EGFr, c-kit, PDGF, FGF, SRC etc. They may also be irreversible inhibitors of protein tyrosine kinases.

Examples of compounds that are similar in structure to those of the present invention are disclosed in the following literatures: WO9717329, WO9722596, WO0047212, WO2002032872, WO2004018430, WO2005073224, WO2005080377, WO2005097134, WO2005097137, WO2005114219, WO2005070891, WO05021553, WO2007084875, WO2007017740, US2005137395, U.S. Pat. No. 7,253,286.

SUMMARY OF THE INVENTION

The present invention relates to compounds of formula I

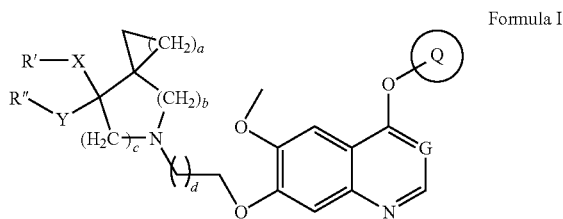

Formula I

Wherein
Ring Q is a bicyclic aryl or a bicyclic heterocyclyl moiety, selected from:

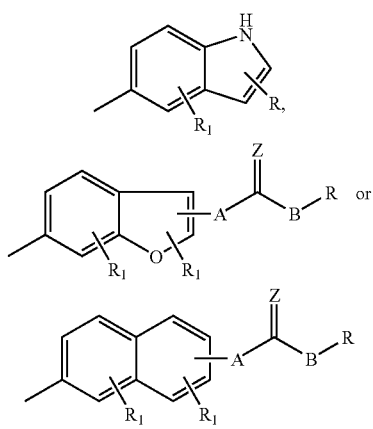

R is each independently selected from H, halogen, halogeno-lower alkyl, lower alkyl, hydroxy, lower alkoxy, lower alkoxyalkoxy, lower alkenyl, lower alkynyl, amino, alkylamino, alkoxyamino, cycloalkyl, cycloalkenyl, aryl or heterocyclyl;

$R_1$ is selected from H, halogen, halogeno-lower alkyl, lower alkyl, hydroxy, lower alkoxy, lower alkoxyalkoxy, lower alkenyl, or lower alkynyl;

A is selected from direct bond of —N(R')—;

B is selected from direct bond, O, —N(R')—, —C(=Z)—, —C(=Z)N(R')—, lower alkylenyl-C(=Z)— or lower alkylenyl-C(=Z)N(R')—;

Z is selected from O or S;

a is selected from 1, 2, 3, 4 or 5;

b, c and d are each independently selected from 1, 2, or 3;

G is selected from C—R, C—(CN) or N;

R' and R" are not presented, when X and Y are selected from (i) X combines Y to be an oxygen or methylene, (ii) X is hydrogen, Y is hydrogen, (iii) X is hydrogen, Y is hydroxy or its optical isomer;

R' and R" are each independently selected from halogeno-lower alkyl, lower alkyl, lower alkoxy, hydroxy, lower alkylhydroxy, when X and Y are selected from (i) X is hydrogen, Y is O, S or its optical isomer, (ii) X and Y are both O or S, or (iii) X is O and Y is S; optionally R' and R" combine to form a 5 to 7 membered ring with X, Y and the said ring can be unsubstituted or substituted independently by up to three substituents, or a pharmaceutically acceptable salt thereof.

DETAILED DESCRIPTION OF THE INVENTION

The present invention is the directed to novel compounds which can inhibit protein tyrosine kinase, and use of these compounds for inhibition of protein tyrosine kinases and angiogenesis in the treatment of a neoplastic or proliferative or chronic inflammatory or angiogenic diseases which are caused by excessive or inappropriate angiogenesis in a mammal in need thereof.

In the compounds of formula (I),

Ring Q is a bicyclic aryl or a bicyclic heterocyclyl moiety, selected from:

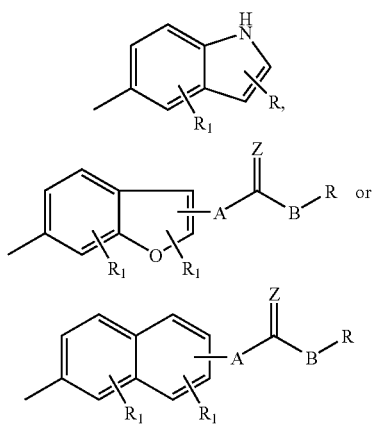

R is each independently selected from H, halogen, halogeno-lower alkyl, lower alkyl, hydroxy, lower alkoxy, lower alkoxyalkoxy, lower alkenyl, lower alkynyl, amino, alkylamino, alkoxyamino, cycloalkyl, cycloalkenyl, aryl or heterocyclyl; preferably selected from H, halogen, halogeno-lower alkyl, lower alkyl;

$R_1$ is selected from H, halogen, halogeno-lower alkyl, lower alkyl, hydroxy, lower alkoxy, lower alkoxyalkoxy, lower alkenyl, or lower alkynyl; preferably selected from H, halogen, halogeno-lower alkyl, lower alkyl;

A is selected from direct bond or —N(R')—; preferably selected from direct bond or —NH—;

B is selected from direct bond, O, —N(R')—, —C(=Z)—, —C(=Z)N(R')—, lower alkylenyl-C(=Z)— or lower alkylenyl-C(=Z)N(R')—; preferably selected from —NH—, —C(=O)—, or —C(=O)NH—;

Z is selected from O or S; preferably O;

a is selected from 1, 2, 3, 4 or 5; preferably 1, 2 or 3;

b, c and d are each independently selected from 1, 2, or 3; preferably 1 or 2;

G is selected from C—R, C—(CN) or N; preferably C—R or N, more preferably CH;

R' and R" are not presented, when X and Y are selected from (i) X combines Y to be an oxygen or methylene, (ii) X is hydrogen, Y is hydrogen, (iii) X is hydrogen, Y is hydroxy or its optical isomer; the preferred moieties are each independently selected from ketone, methylene or hydroxy or optical isomer of said hydroxy;

R' and R" are each independently selected from halogeno-lower alkyl, lower alkyl, lower alkoxy, hydroxy, lower alkylhydroxy, when X and Y are selected from (i) X is hydrogen, Y is O, S or its optical isomer, (ii) X and Y are both O or S, or (iii) X is O and Y is S; optionally R' and R" combine to form a 5 to 7 membered ring with X, Y and the said ring can be unsubstituted or substituted independently by up to three substituents, the preferred moieties are each independently selected from alkoxy or optical isomers of said alkoxy, cyclic ketal, cyclic thioketal, or cyclic thioxolane which may be unsubstituted or substituted with lower alkyl, aryl or heterocyclyl;

or a pharmaceutically acceptable salt thereof.

The term "halogen", as used herein, unless otherwise indicated, includes fluoro, chloro, bromo or iodo such as fluoro and chloro.

The term "halogen-lower alkyl", as used herein, unless otherwise indicated, includes 1 to 6 halogen substituted alkyl, such as trifluoromethyl.

The term "lower alkyl", as used herein, unless otherwise indicated, includes 1 to 6 saturated monovalent hydrocarbon radicals having straight or branched moieties, including, but not limited to, methyl, ethyl, n-propyl, iso-propyl, n-butyl, sec-butyl, tert-butyl, and the like.

The term "lower alkenyl", as used herein, unless otherwise indicated, includes lower alkyl groups, as defined above, having at least one carbon-carbon double bond, such as —CH$_2$—CH=CH$_2$.

The term "lower alkynyl", as used herein, unless otherwise indicated, includes lower alkyl groups, as defined above, having at least one carbon-carbon triple bond, such as —CH$_2$—C≡CH.

The term "lower alkoxy", as used herein, unless otherwise indicated, includes —O-lower alkyl groups wherein lower alkyl is as defined above, such as methoxy and ethoxy.

The term "lower alkoxyalkoxy", as used herein, unless otherwise indicated, include —O-lower alkyl-O-lower alkyl groups wherein lower alkyl is as defined above, such as —OCH$_2$CH$_2$OCH$_3$.

The term "lower alkylenyl", as used herein, unless otherwise indicated, includes 1 to 6 saturated —CH$_2$— radicals.

The term "amino", as used herein, unless otherwise indicated, includes —NH$_2$ group, —NH—lower alkyl group, or —N(lower alkyl)$_2$ group wherein lower alkyl is as defined above, such as methylamino and dimethylamino.

The term "alkyamino", as used herein, unless otherwise indicated, includes-lower alkyl-$NH_2$ group, -lower alkyl-NH-lower alkyl group, or -lower alkyl-N(lower alkyl)$_2$ group wherein lower alkyl is as defined above, such as —$CH_2CH_2NHCH_3$.

The term "alkoxyamino", as used herein, unless otherwise indicated, includes —O-lower alkyl-$NH_2$ group, —O-lower alkyl-NH-lower alkyl group, or —O-lower alkyl-N(lower alkyl)$_2$ group wherein lower alkyl is as defined above, such as —$OCH_2CH_2NHCH_3$.

The term "aryl", as used herein, unless otherwise indicated, includes an organic radical derived from an aromatic hydrocarbon by removal of one hydrogen, such as phenyl or naphthyl, preferably phenyl, and is unsubstituted or substituted by one or two substituents, selected from halogen, halogeno-lower alkyl, lower alkyl, lower alkenyl, lower alkynyl, cyano, lower alkylcyano, hydroxy, lower alkoxy, carboxy, carboxyalkyl, amino, carbamoyl, cabamate, ureido, mercapto, sulfo, lower alkylsulfinyl, lower alkanesulfonyl, sulfonamide; aryl includes one aromatic ring fused with an aliphatic ring, such as a saturated or partially saturated ring, such as tetrahydronaphthyl.

The term "heterocyclyl", as used herein, unless otherwise indicated, includes non-aromatic, single and fused rings suitably containing up to four heteroatoms in each ring, each of which independently selected from O, N and S, and which rings, may be unsubstituted or substituted independently by, for example, up to three substituents. Each heterocyclic ring suitably has from 4 to 7, preferably 5 or 6, ring atoms. A fused heterocyclic ring system may include carbocyclic rings and need include only one heterocyclic ring which may be partially saturated or saturated. The heterocyclyl includes mono, bicyclic and tricyclic heteroaromatic ring systems comprising up to four, preferably 1 or 2, heteroatoms each selected from O, N and S. Each ring may have from 4 to 7, preferably 5 or 6, ring atoms. A bicyclic or tricyclic ring system may include a carbocyclic ring. Carbocyclic ring includes cycloalkyl, cycloalkenyl or aryl ring. examples of heterocyclyl groups include but not limited: azetidine, pyrrolidine, pyrrolidione, piperidine, piperidinone, piperazine, morpholine, oxetane, tetrahydrofuran, tetrahydropyran, imidazolidine, pyrazolidine and hydantoin, pyrrole, indole, pyrazole, indazole, trizole, benzotrizole, imidazole, benzoimdazole, thiophene, benzothiophene, thiozole, benzothiozole, furan, benzofuran, oxazole, bezoxazole, isoxazole, tetrazole, pyridine, pyrimidine, trizine, quinoline, isoquinoline, quinazoline, indoline, indolinone, benzotetrahydrofuran, tetrahydroquinoline, tetrahydroisoquinoline, methylene-dioxyphenyl. The heterocyclic and heterocyclic rings may be optionally substituted and substituents selected from the group defined above as substituents for aryl.

The term "cycloalkyl", as used herein, unless otherwise indicated, includes cyclic radicals having from three to eight ring carbon atoms, including, but not limited to cyclopropyl, cyclobutyl, cyclopentyl, cyclohexyl, and the like. The cycloalkyl groups may be optionally substituted one or more times, substituents selected from the group defined above as substituents for aryl, preferably halogen, lower alkyl.

The term "cycloalkenyl", as used herein, unless otherwise indicated, includes cycloalkyl groups, as defined above, having at least one carbon-carbon double bond.

Several in vitro tyrosine kinase inhibition activities can be measured according to the description in Rewcastle, G W, J. Med. Chem. 1996, 39, 918-928 and Edwards M, International Biotechnology Lab 5 (3), 19-25, 1987. Oncogene, 1990, 5:519-524. The Baculovirus Expression System: A Laboratory Guide, L. A. King 1992. Sambrook et al, 1989, Molecular cloning-A Laboratory Manual, 2nd edition, Cold Spring Harbour Laboratory Press. O'Reilly et al, 1992, Baculovirus Expression Vectors-A Laboratory Manual, W. H. Freeman and Co, New York.

Receptor tyrosine kinase can be obtained in partially purified form from A-431 cells similar to those described by Carpenter et al., J. Biol. Chem., 1979, 254, 4884, Cohen et al., J. Biol. Chem., 1982, 257, 1523 and by Braun et al., J. Biol. Chem., 1984, 259, 2051. Some of these tests can also be contracted with Millipore Upstate Ltd for screening.

Compounds listed in examples have IC50 range from sub-nanomole to micromole inhibition activities towards various receptor tyrosine kinases.

The following in vitro results are activities of example compounds in present invention against human tumor NSCLC A549 cell line and colon LOVO cell line in MTT assay.

|            | A549 (IC50, μM) | LOVO (IC50, μM) |
|------------|-----------------|-----------------|
| Example 1  | 0.09            | 0.2             |
| Example 2  | 0.1             | 0.3             |
| Example 3  | 0.1             | 0.4             |
| Example 4  | 0.08            | 0.4             |
| Example 5  | 0.1             | 0.4             |
| Example 6  | 0.08            | 0.4             |
| Example 7  | 0.09            | 0.2             |
| Example 8  | 0.1             | 0.3             |
| Example 9  | 0.1             | 0.4             |
| Example 10 | 0.1             | 0.4             |
| Example 11 | 0.2             | 0.7             |
| Example 12 | 0.3             | 0.9             |
| Example 13 | 0.2             | 0.9             |
| Example 14 | 0.2             | 0.7             |
| Example 15 | 0.3             | 0.9             |
| Example 16 | 0.2             | 0.7             |
| Example 17 | 0.3             | 0.9             |
| Example 18 | 0.5             | 0.8             |
| Example 19 | 0.2             | 0.7             |
| Example 20 | 0.3             | 0.9             |
| Example 21 | 0.8             | 1.1             |
| Example 22 | 0.7             | 1.1             |
| Example 23 | 0.8             | 1.2             |
| Example 24 | 1.0             | 1.5             |
| Example 25 | 0.3             | 0.9             |
| Example 26 | 0.8             | 1.1             |
| Example 27 | 0.4             | 0.9             |
| Example 28 | 1.0             | 1.5             |
| Example 29 | 0.3             | 0.9             |
| Example 30 | 0.9             | 1.0             |

Animal antitumor activity testing can be conducted as follows:

The compounds were mixed with tween 80 and 0.5% CMC as suspensions. Nude female mice (17-19 g) were used. Ascitic fluid of human LOVO colon cancer (or mice HAC liver cancer) was diluted with 0.9% NaCl solution (1:4), and injected 0.2 ml to each mouse subcutaneously. The whole animals (n=12) were separated even as test and control group randomly. The test group was administered drugs orally at 0.5-500 mg/Kg dosage once a day from second day after injection of tumor for eighteen days. The animals were sacrificed at 21st days and each tumor was extracted and weighted for both groups and calculated the difference in percentage for antitumor activity.

A compound of formula I can be administered alone or in combination with one or more other therapeutic agents, possible combination therapy taking the form of fixed combinations or administration of a compound of the invention and one or more other therapeutic agents being staggered or given independently of one another, or the combined administration of fixed combinations and one or more other therapeutic agents.

A compound of formula I can besides or in addition be administered especially for tumor therapy in combination with chemotherapy, radiotherapy, surgical intervention, or a combination of these. Long term therapy is equally possible as is adjuvant therapy in the context of other treatment strategies, as described above. Other possible treatments are therapy to maintain the patient's status after tumor regression, or even chemopreventive therapy, for example in patients at risk.

A compound according to the invention is not only for management of humans, but also for the treatment of other warm-blooded animals, for example of commercially useful animals. Such a compound may also be used as a reference standard in the test systems described above to permit a comparison with other compounds.

Salts are especially the pharmaceutically acceptable salts of compounds of formula I. Suitable pharmaceutically acceptable salts will be apparent to those skilled in the art and include those described in J. Pharm. Sci., 1977, 66, 1-19, such as acid addition salts formed with inorganic acid e.g. hydrochloric, hydrobromic, sulphuric, nitric or phosphoric acid; and organic acids e.g. succinic, maleic, acetic, fumaric, citic, tartaric, benzoic, p-toluenesulfonic, methanesulfonic or naphthalenesulfonic acid. Other salts may be used, for example in the isolation or purification of compounds of formula (I) and are included within the scope of this invention.

The compounds of this invention may be in crystalline or non-crystalline form, and, if crystalline, may optionally be hydrated or solvated. This invention includes within its scope stoichiometric hydrates as well as compounds containing variable amount of water.

The invention extents to all isomeric forms including stereoisomers and geometic isomers of the compounds of formula (I) including enantimers and mixtures thereof e.g. racemates. The different isomeric forms may be separated or resolved one from the other by conventional methods, or any given isomer may be obtained by conventional synthetic methods or by stereospecific or asymmetric syntheses.

Those skilled in the art will recognize various synthetic methodologies that may be employed to prepare non-toxic pharmaceutically acceptable prodrugs of the compounds encompassed by Formula I. Those skilled in the art will recognize a wide variety of non-toxic pharmaceutically acceptable solvents that may be used to prepare solvates of the compounds of the invention, such as water, ethanol, mineral oil, vegetable oil, and dimethylsulfoxide.

The compounds of general Formula I may be administered orally, topically, parenterally, by inhalation or spray or rectally in dosage unit formulations containing conventional non-toxic pharmaceutically acceptable carriers, adjuvants and vehicles. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The compounds may also be administered in the form of suppositories for rectal or vaginal administration of the drug. These compositions can be prepared by mixing the drug with a suitable non-irritating excipient which is solid at ordinary temperatures but liquid at the rectal or vaginal temperature and will therefore melt in the rectum or vagina to release the drug. Such materials include cocoa butter and polyethylene glycols.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the invention may also be administered transdermally using methods know to those skilled in the art (see, for example: Chien; "transdermal Controlled Systemic Medications"; Marcel Dekker, Inc.; 1987. Lipp et al. WO 94/04157 3, Mar. 1994).

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition may also be added to the animal feed or drinking water. It will be convenient to formulate these animal feed and drinking water compositions so that the animal takes in an appropriate quantity of the composition along with its diet. It will also be convenient to present the composition as a premix for addition to the feed or drinking water.

For all regimens of use disclosed herein for compounds of formula I, the daily oral dosage regimen will preferably be from 0.01 to 200 mg/Kg of total body weight. The daily dosage for administration by injection, including intravenous, intramuscular, subcutaneous and parenteral injections, and use of infusion techniques will preferably be from 0.01 to 200 mg/Kg of total body weight. The daily rectal dosage regimen will preferably be from 0.01 to 200 mg/Kg of total body weight. The daily vaginal dosage regimen will preferably be from 0.01 to 200 mg/Kg of total body weight. The daily topical dosage regimen will preferably be from 0.01 to 200 mg administered between one to four times daily. The transdermal concentration will preferably be that required to maintain a daily dose of from 0.0 1 to 200 mg/Kg. The daily inhalation dosage regimen will preferably be from 0.01 to 200 mg/Kg of total body weight.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have certain pharmacological properties. Such properties include, but are not limited to oral bioavailability, low toxicity, low serum protein binding and desirable in vitro and in vivo half-lives.

Assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (Journal of Chromatography B (1996) volume 677, pages 1-27).

Compound half-life is inversely proportional to the frequency of dosage of a compound. In vitro half-lifes of compounds may be predicted from assays of microsomal half-life as described by Kuhnz and Gieschen [Drug Metabolism and Disposition, (1998), 26, 1120-1127].

Representative illustrations of the preparation of the present invention are given in Scheme I-Scheme IV. Those having skill in the art will recognize that the starting materials may be varied and additional steps may be employed to produce compounds encompassed by the present invention.

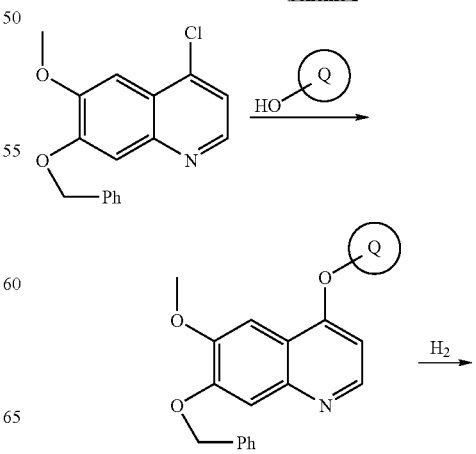

Scheme I

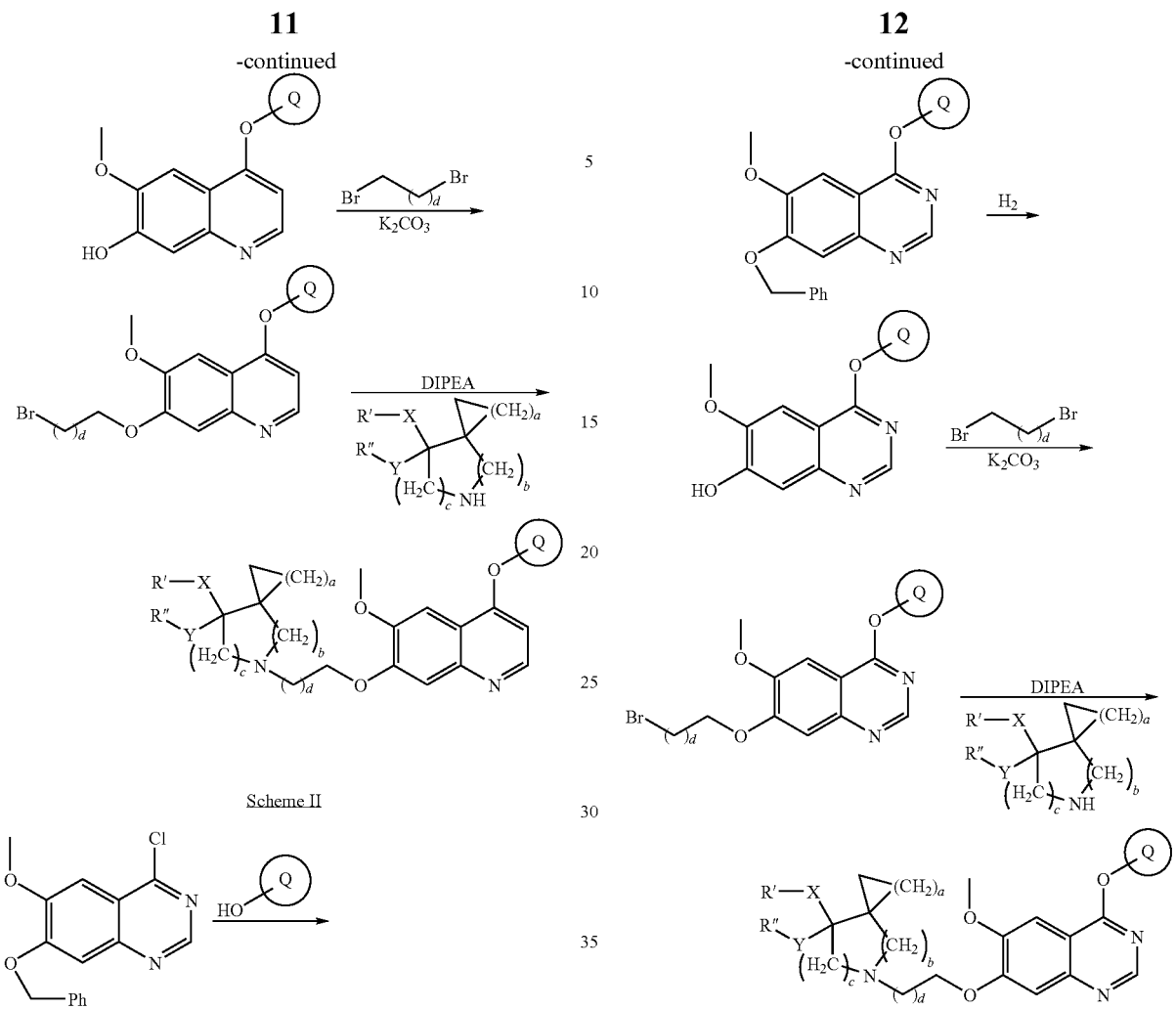
Scheme II
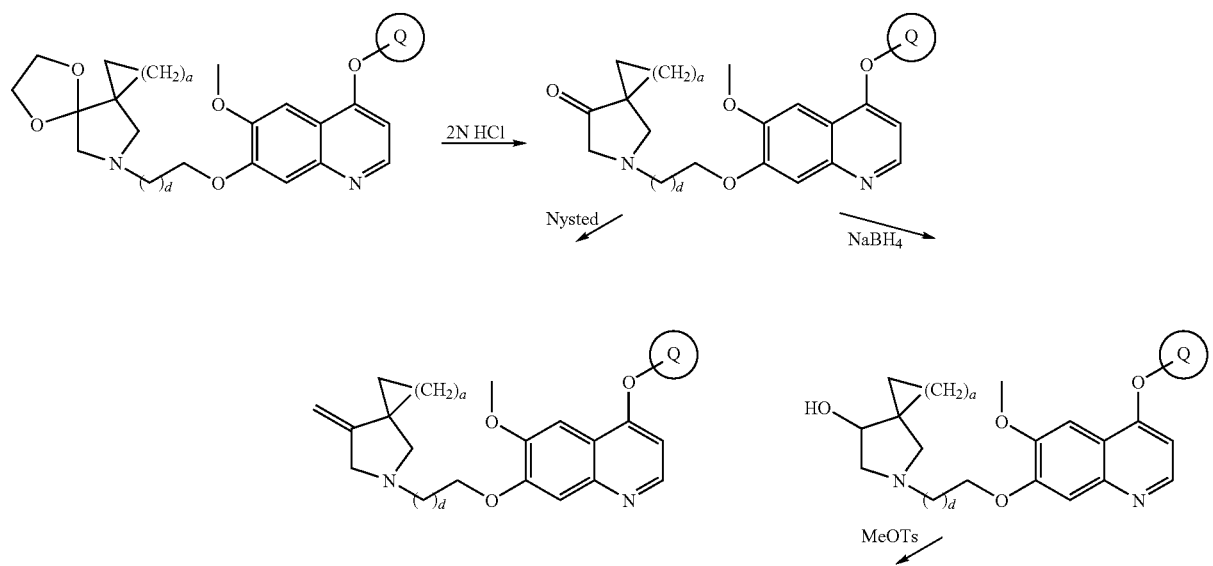
Scheme III

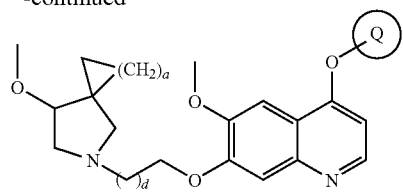
10
Scheme IV
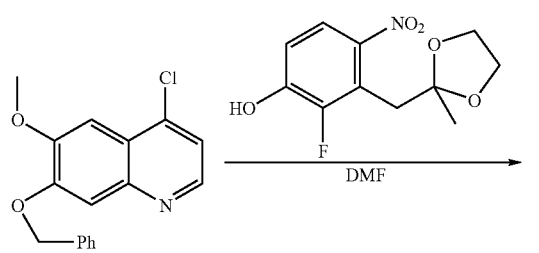
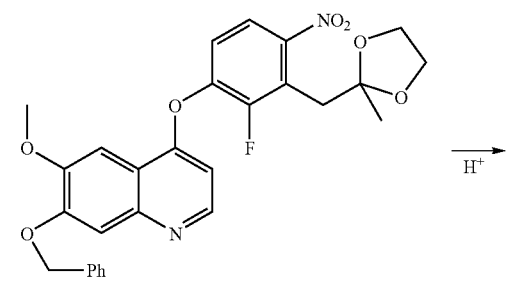
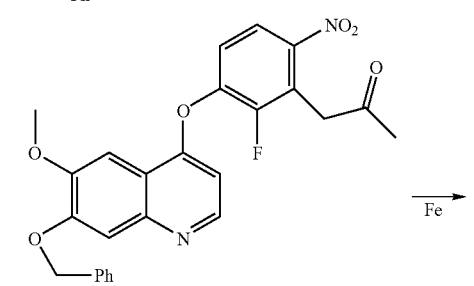
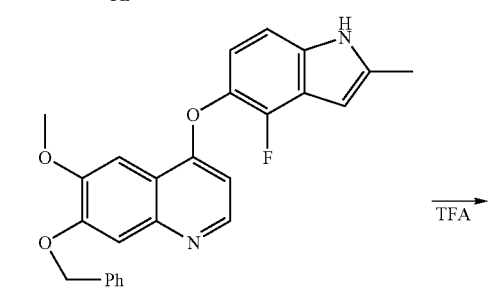
-continued
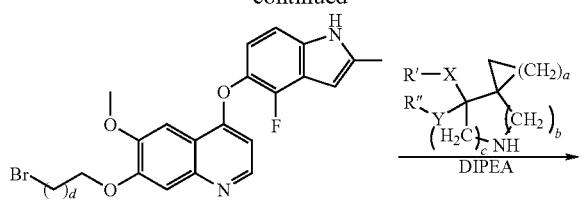
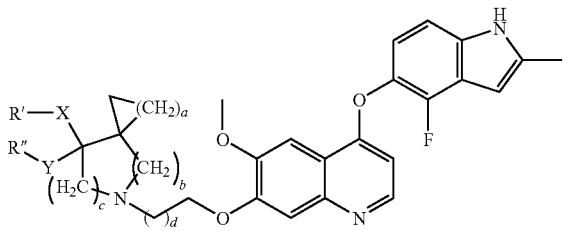
Scheme V
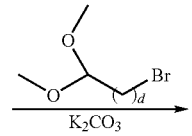
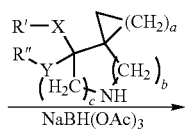

-continued

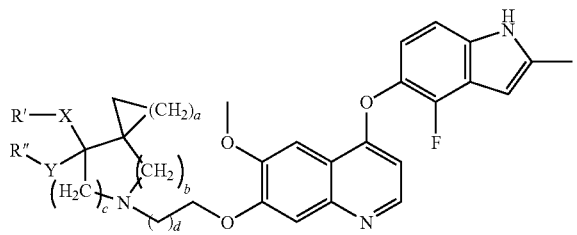

The following examples of Formula II, but not limited, can be prepared similarly according to the methods described in Scheme I-Scheme V.

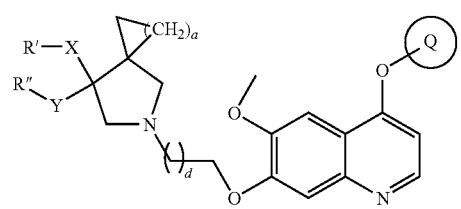

Formula II

Wherein

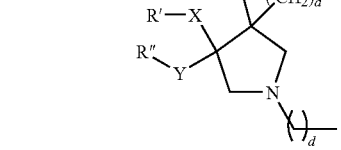

is independently selected from:

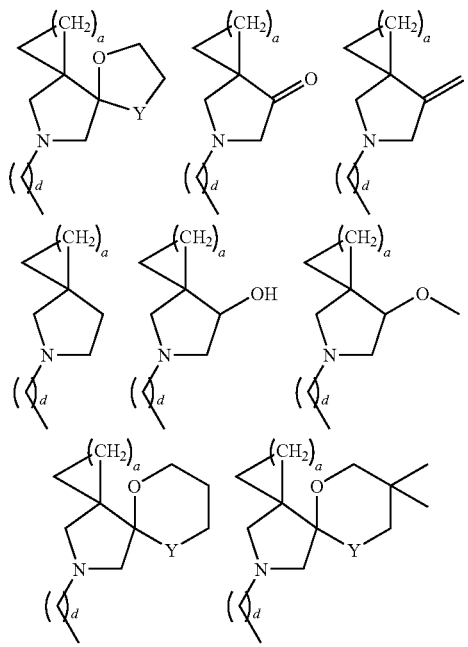

-continued

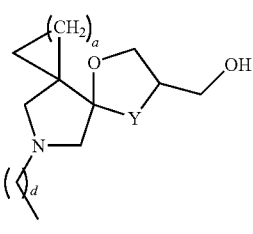

a or d are 1, 2, or 3; Y is O or S

Ring Q is independently selected from

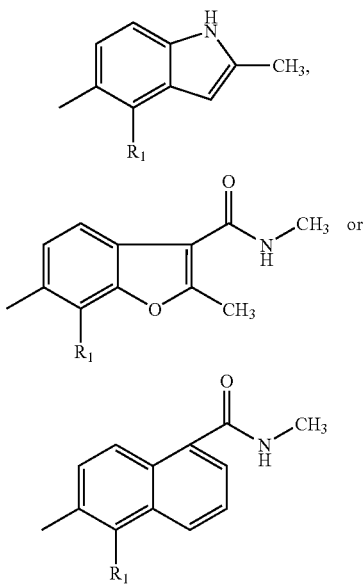

$R_1$ is H or F or a pharmaceutically acceptable salt thereof.

The following examples, but not limited, can also be prepared similarly according to the methods described in Scheme I-Scheme V.

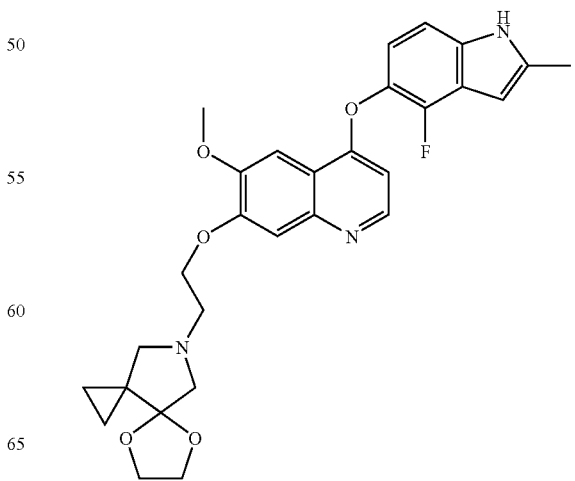

| 17 | 18 |
|---|---|
| -continued | -continued |
| 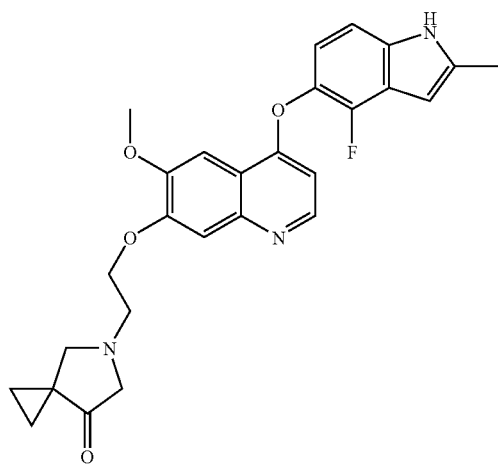 | 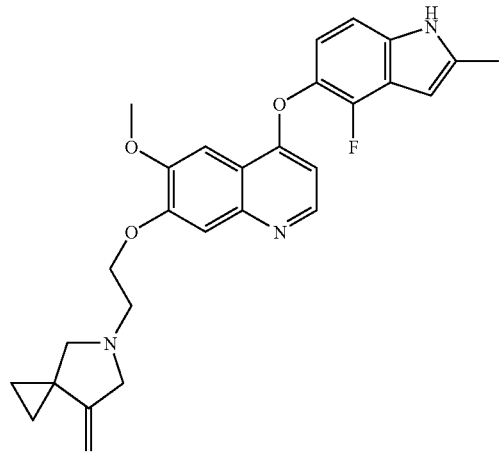 |
| 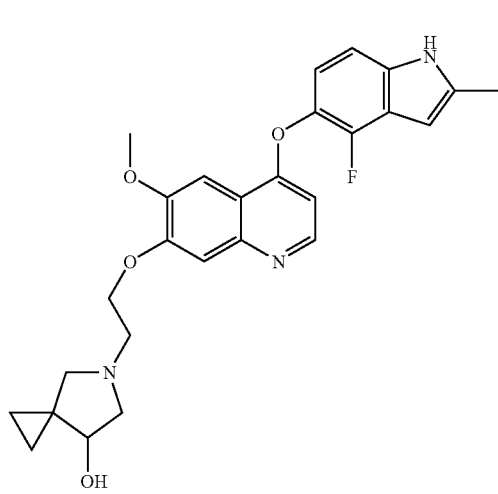 | 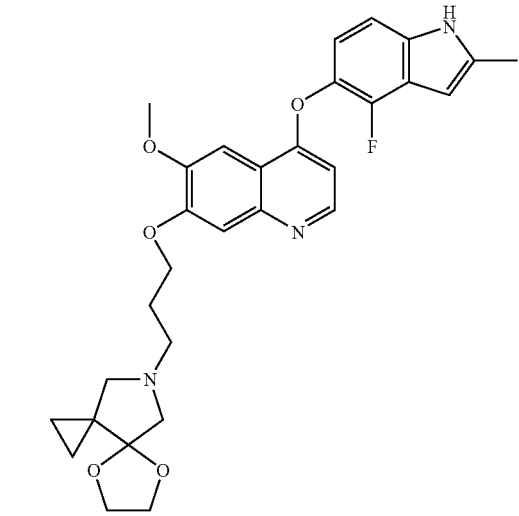 |
| 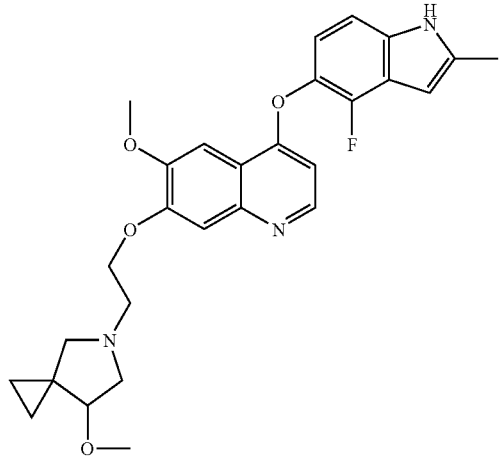 | 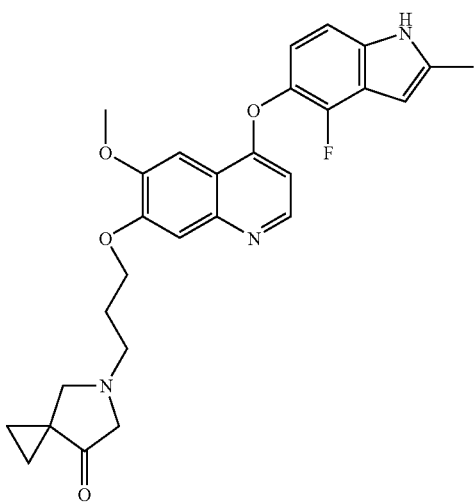 |

19
-continued
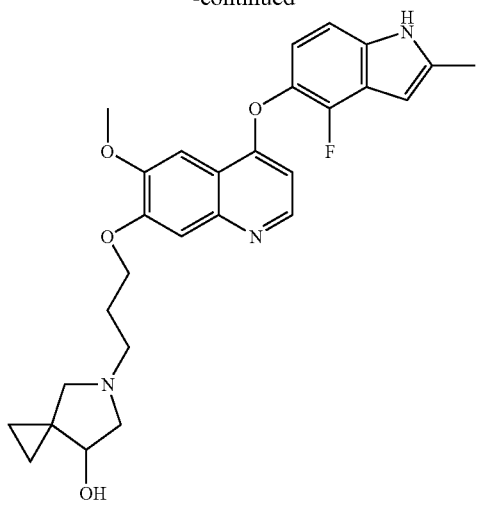
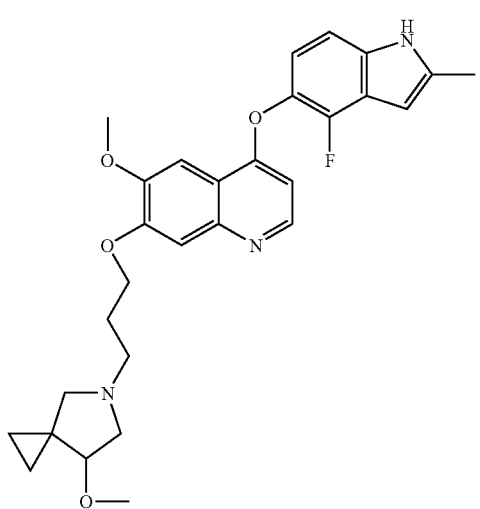
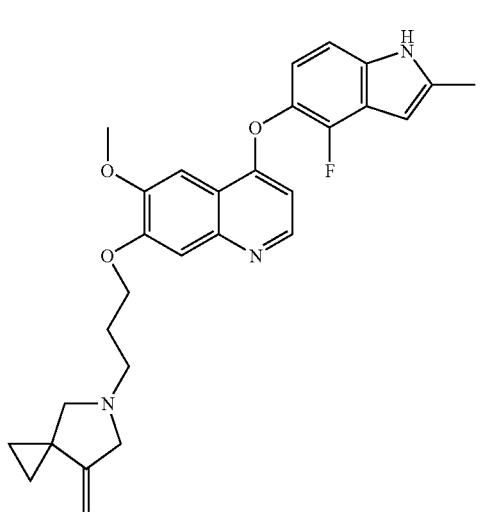
20
-continued
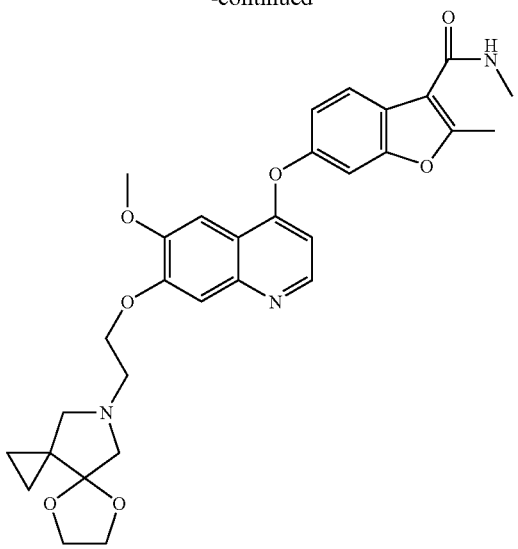
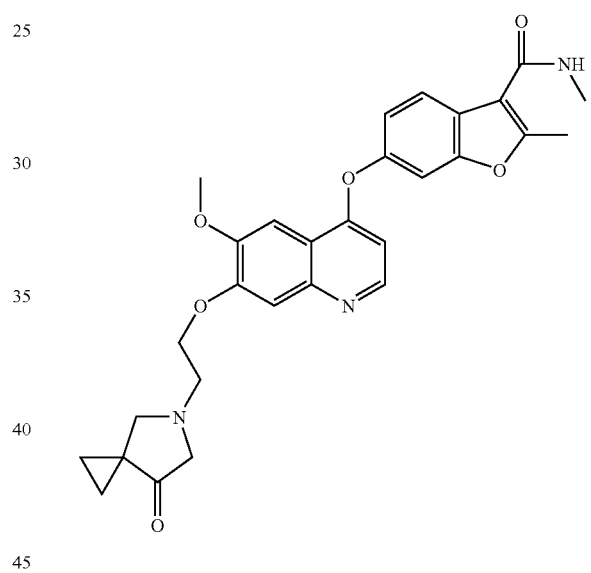
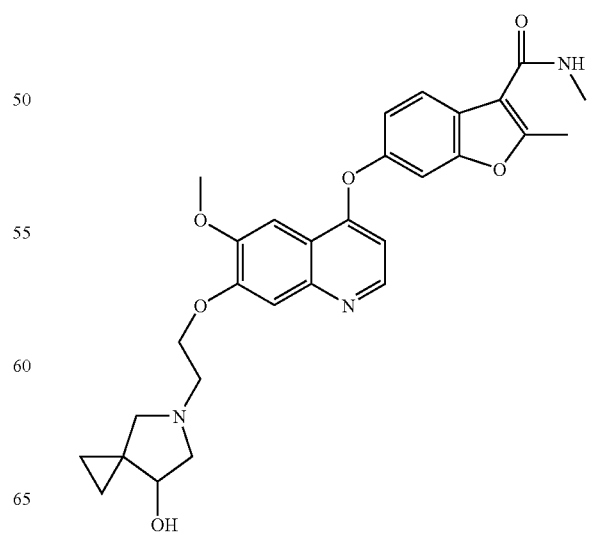

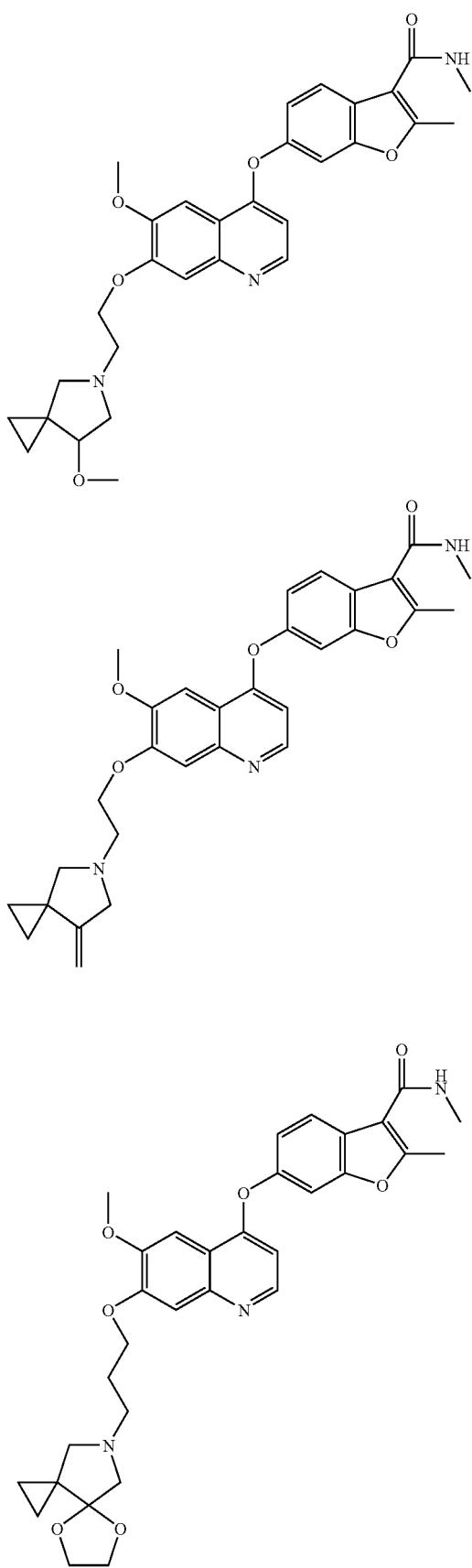

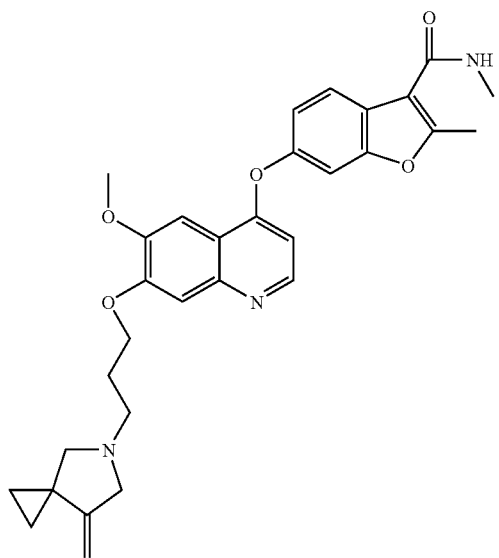
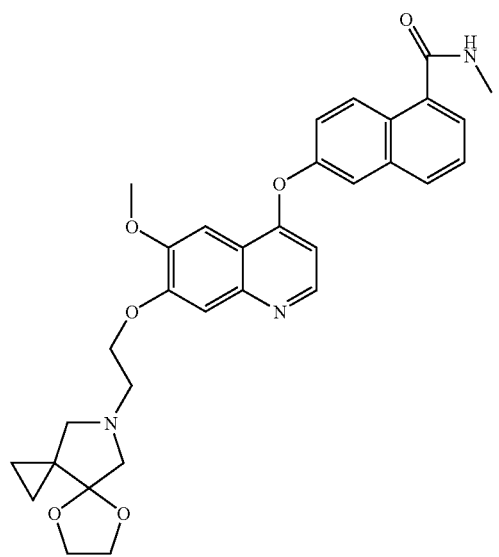
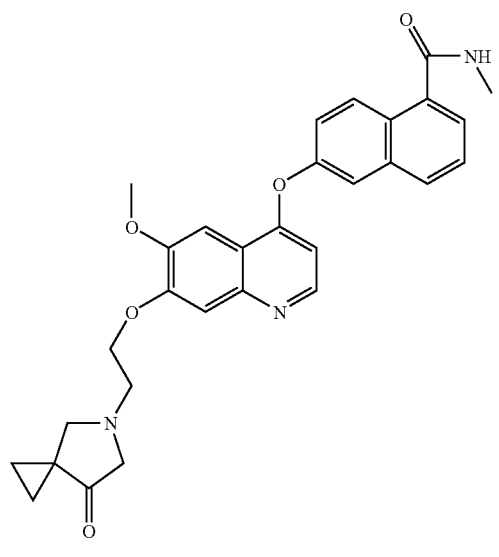
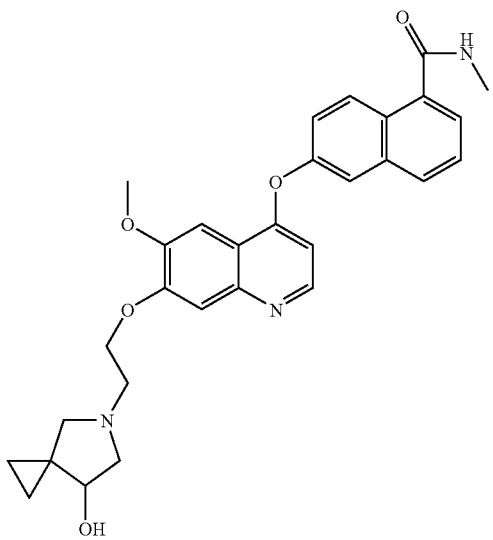
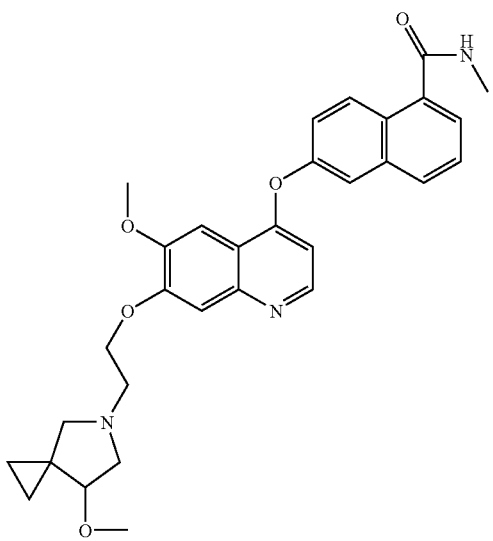
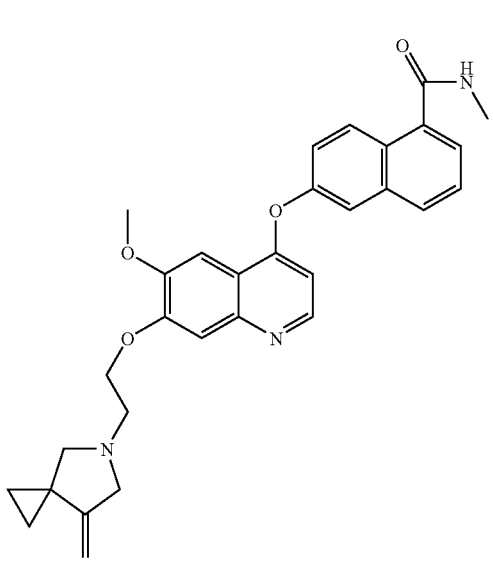

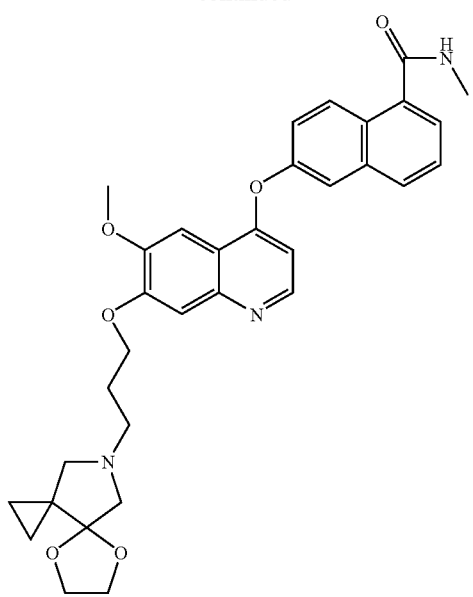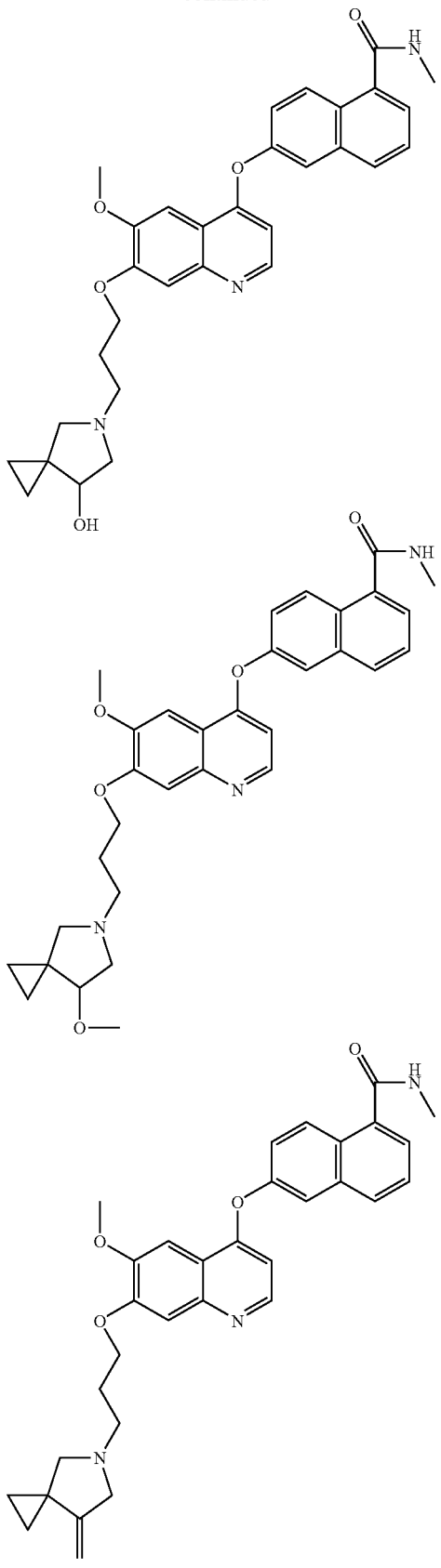
or a pharmaceutically acceptable salt thereof.

In some cases protection of certain reactive functionalities may be necessary to achieve some of above transformations. In general the need for such protecting groups will be apparent to those skilled in the art of organic synthesis as well as the conditions necessary to attach and remove such groups. Those skilled in the art will recognize that in certain instances it will be necessary to utilize different solvents or reagents to achieve some of the above transformations.

The disclosures in this application of all articles and references, including patents, are incorporated herein by reference in their entirety.

The invention is illustrated further by the following examples, which are not to be construed as limiting the invention in scope or spirit to the specific procedures described in them.

The starting materials are and various intermediates may be obtained from commercial sources, prepared from commercially available organic compounds, or prepared using well known synthetic methods.

Representative methods for preparing intermediates of the invention are set forth below in the examples.

The following abbreviations have been used and others are all standard chemical formula representation.

EtOH: ethanol, MeOH: methanol, RT: room temperature, DIPEA: diisopropylethylamine, DCM: Dichloromethane, DMF: N,N-dimethylformamide, DMAP: dimethylaminopyridine, EtOAc: ethyl acetate, $Et_2O$: Dimethyl Ether, MsCl: Methanesulfonyl chloride, eq: equivalent, g: gram, mg: milligram, ml: milliliter, μl: microliter, min: minutes

EXAMPLE 1

4-(4-Fluoro-2-methyl-1H-indol-5-yloxy)-6-methoxy-7-[2-(5,8-Dioxa-10-azadispiro[2.0.4.3]-undecane)ethoxy]quinoline Preparation of 4-(4-fluoro-2-methyl-1H-indol-5-yloxy)-6-methoxy-7-benzyloxyquinoline Method A:
4-Chloro-7-benzyloxy-6-methoxy-quinoline (WO2008112407, 1.5 g) was mixed with DMAP (1.5 eq), 2-methyl-4-fluoro-5-hydroxyindole (WO0047212) (1 eq) in dioxane (20 ml). The reaction was refluxed for three days and diluted with EtOAc, water and extracted with EtOAc three times. The combined organic layer was washed with water, brine and dried. The solution was evaporated and purified with silica gel column to give 4-(4-fluoro-2-methyl-1H-indol-5-yloxy)-6-methoxy-7-benzyloxyquinoline (600 mg).

Method B:
4-Chloro-7-benzyloxy-6-methoxy-quinoline (WO2008112407, 1.5 g) was mixed with 3-(2,2-dimethoxypropyl)-2-fluoro-4-nitrophenol (WO0047212) (1.5 eq) in dioxane (30 ml). The reaction was refluxed for three days and diluted with EtOAc, water and extracted with EtOAc three times. The combined organic layer was washed with water, brine and dried. The solution was evaporated and purified with silica gel column to give 7-(benzyloxy)-4-(3-(2,2-dimethoxypropyl)-2-fluoro-4-nitrophenoxy)-6-methoxyquinoline (650 mg). This product was mixed with 2NHCl (3 ml) and acetone (30 ml) and refluxed for 6 hours. The reaction was diluted with EtOAc and neutralized with saturated $NaHCO_3$, further extracted with EtOAc three times. The combined organic layer was washed with water, brine and dried. The solution was evaporated and purified with silica gel column to give 1-(3-(7-(benzyloxy)-6-methoxyquinolin-4-yloxy)-2-fluoro-6-nitrophenyl)propan-2-one (500 mg) which was mixed with iron (500 mg) and $NH_4Cl$ (50 mg) in EtOH/$H_2O$ (20 ml, 4/1). The reaction was refluxed for 4 hours, filter through Celite and evaporated. The residue was extracted with EtOAc three times. The combined organic layer was washed with water, brine and dried. The solution was evaporated and purified with silica gel column to give 4-(4-fluoro-2-methyl-1H-indol-5-yloxy)-6-methoxy-7-benzyloxyquinoline (250 mg).

4-(4-Fluoro-2-methyl-1H-indol-5-yloxy)-6-methoxy-7-benzyloxyquinoline (600 mg) was mixed with $HCONH_4$ (600 mg) and Pd/C (10%, 100 mg) followed by refluxing 30 min. The reaction was filtered while it was hot and the filtrate was evaporated and washed with water followed by filtration to give 4-(4-fluoro-2-methyl-1H-indol-5-yloxy)-6-methoxy-7-hydroxyquinoline (400 mg).

Preparation of Title Compound
Method C:
4-(4-Fluoro-2-methyl-1H-indol-5-yloxy)-6-methoxy-7-hydroxyquinoline (400 mg) was mixed with 1,2-dibromoethane (2 eq) and $K_2CO_3$ (2 eq) in DMF (5 ml). The reaction was heated at 100° C. for 5 hours and diluted with EtOAc, water and extracted with EtOAc three times. The combined organic layer was washed with water, brine and dried. The solution was evaporated and purified with silica gel column. The product was mixed with NaI (250 mg) in acetonitrile (15 ml) and refluxed for 30 min. The reaction was cooled, DIPEA (500 μL) and 5,8-Dioxa-10-azadispiro[2.0.4.3]-undecane (300 mg) were added into the reaction which was refluxed overnight. The reaction was diluted with EtOAc, water and extracted with EtOAc three times. The combined organic layer was washed with water, brine and dried. The solution was evaporated and purified with silica gel column to give title compound (150 mg). Mass: (M+1), 520

Method D:
4-(4-Fluoro-2-methyl-1H-indol-5-yloxy)-6-methoxy-7-hydroxyquinoline (400 mg) was mixed with 2-bromo-1,1-dimethoxyethane (2 eq) and $K_2CO_3$ (2 eq) in DMF (5 ml). The reaction was heated at 100° C. for 8 hours and diluted with EtOAc, water and extracted with EtOAc three times. The combined organic layer was washed with water, brine and dried. The solution was evaporated and purified with silica gel column. The product was mixed with 1NHCl (2 ml) in EtOH (10 ml) and refluxed for 5 hours. The reaction was evaporated and neutralized with saturated $NaHCO_3$, further extracted with EtOAc three times. The combined organic layer was washed with water, brine and dried. The solution was evaporated and purified with silica gel column to give the aldehye adduct (400 mg) which was mixed with 5,8-Dioxa-10-azadispiro[2.0.4.3]-undecane (200 mg) with NaBH(OAc)3 (2 eq) in DCM (10 ml). The reaction was stirred at RT for 2 hours then diluted with EtOAc, water and extracted with EtOAc three times. The combined organic layer was washed with water, brine and dried. The solution was evaporated and purified with silica gel column give title compound (250 mg). Mass: (M+1), 520,

EXAMPLE 2

5-(2-(4-(4-Fluoro-2-methyl-1H-indol-5-yloxy)-6-methoxyquinolin-7-yloxy)ethyl)-5-azaspiro[2.4]-heptan-7-one The above product from Example 1 (100 mg) was mixed with 1N HCl (4 ml) and acetone (20 ml). The reaction was refluxed overnight and evaporated. The solution was basified with 2N NaOH and extracted with EtOAc. The combined organic layer was washed with $H_2O$ followed by brine, dried over Na$_2$SO$_4$ and evaporated. The residue was purified by column chromatography to give title compound (75 mg). Mass: (M+1), 476

EXAMPLE 3

5-(2-(4-(4-fluoro-2-methyl-1H-indol-5-yloxy)-6-methoxyquinolin-7-yloxy)ethyl)-5-azaspiro[2.4]-heptan-7-ol The above product from Example 2 (75 mg) was dissolved into MeOH (8 ml) and stirred at RT. NaBH$_4$ (75 mg) was added to the reaction and stirred at RT for 30 min. The reaction was evaporated and purified by column chromatography to give title compound (60 mg). Mass: (M+1), 478

EXAMPLE 4

4-(4-Fluoro-2-methyl-1H-indol-5-yloxy)-6-methoxy-7-(2-(7-methoxy-5-azaspiro[2.4]heptan-5-yl)ethoxy)quinoline The above product from Example 2 (60 mg) was dissolved into DMF (4 ml) and cooled at 0° C. NaH (1.1 eq) was added to the reaction and stirred for 10 minutes. To the reaction was added TsOMe (1.2 eq), the solution was heated at 80° C. for two hours. The reaction was quenched with water and extracted with EtOAc followed by washing with water, then brine and dried over Na$_2$SO$_4$. The solution was evaporated and purified by silica column to give the titled product. Mass: (M+1), 492

EXAMPLE 5

4-(4-Fluoro-2-methyl-1H-indol-5-yloxy)-6-methoxy-7-(2-(7-methylene-5-azaspiro[2.4]heptan-5-yl)ethoxy)quinoline The above product from Example 2 (50 mg) was dissolved into anhydrous tetrahydrofuran (5 ml) and Nysted reagent (1.5 eq, 20% solution) was added to the reaction. The reaction was stirred at RT for two days and quenched with NH$_4$Cl solution and extracted with EtOAc followed by washing with water, then brine and dried over Na$_2$SO$_4$ and purified with silica gel column to give the titled compound. Mass: (M+1), 474

EXAMPLE 6

4-(4-fluoro-2-methyl-1H-indol-5-yloxy)-6-methoxy-7-[3-(5,8-Dioxa-10-azadispiro[2.0.4.3]-undecane)propoxy]quinoline The title compound was prepared by similar manner to Example 1, by use of 1,3-dibromopropane instead of 1,2-dibromoethane in Method C; or by use of 3-bromo-1,-dimethoxypropane instead of 2-bromo-1,1-dimethoxy-ethane in Method D. Mass: (M+1), 534

EXAMPLE 7

5-(3-(4-(4-Fluoro-2-methyl-1H-indol-5-yloxy)-6-methoxyquinolin-7-yloxy)propyl)-5-azaspiro[2.4]-heptan-7-one The title compound was prepared by similar manner to Example 2, starting from the compound of Example 6. Mass: (M+1), 490

EXAMPLE 8

5-(3-(4-(4-Fluoro-2-methyl-1H-indol-5-yloxy)-6-methoxyquinolin-7-yloxy)propyl)-5-azaspiro[2.4]-heptan-7-ol The title compound was prepared by similar manner to Example 3, starting from the compound of Example 7. Mass: (M+1), 492

EXAMPLE 9

4-(4-Fluoro-2-methyl-1H-indol-5-yloxy)-6-methoxy-7-(3-(7-methoxy-5-azaspiro[2.4]heptan-5-yl)propoxy)quinoline The title compound was prepared by similar manner to Example 4, starting from the compound of Example 8. Mass: (M+1), 506

EXAMPLE 10

4-(4-Fluoro-2-methyl-1H-indol-5-yloxy)-6-methoxy-7-(3-(7-methylene-5-azaspiro[2.4]heptan-5-yl)propoxy)quinoline The title compound was prepared by similar manner to Example 5, starting from the compound of Example 7. Mass: (M+1), 488

EXAMPLE 11

6-(6-Methoxy-7-[2-(5,8-Dioxa-10-azadispiro[2.0.4.3]undecane)ethoxy]quinolin-4-yloxy)-N,2-dimethyl-benzofuran-3-carboxamide The title compound was prepared by similar manner to Example 1, by use of 6-hydroxy-N,2-dimethylbenzofuran-3-carboxamide instead of 2-methyl-4-fluoro-5-hydroxyindole in Method A. Mass: (M+1), 560

EXAMPLE 12

6-(6-Methoxy-7-(2-(7-oxo-5-azaspiro[2.4]heptan-5-yl)ethoxy)quinolin-4-yloxy)-N,2-dimethylbenzofuran-3-carboxamide The title compound was prepared by similar manner to Example 2, starting from the compound of Example 11. Mass: (M+1), 516

EXAMPLE 13

6-(7-(2-(7-Hydroxy-5-azaspiro[2.4]heptan-5-yl)ethoxy)-6-methoxyquinolin-4-yloxy)-N,2-dimethyl-benzofuran-3-carboxamide The title compound was prepared by similar manner to Example 3, starting from the compound of Example 12. Mass: (M+1), 518

EXAMPLE 14

6-(6-Methoxy-7-(2-(7-methoxy-5-azaspiro[2.4]heptan-5-yl)ethoxy)quinolin-4-yloxy)-N,2-dimethylbenzofuran-3-carboxamide The title compound was prepared by similar manner to Example 4, starting from the compound of Example 13. Mass: (M+1), 532

EXAMPLE 15

6-(6-Methoxy-7-(2-(7-methylene-5-azaspiro[2.4]heptan-5-yl)ethoxy)quinolin-4-yloxy)-N,2-dimethylbenzofuran-3-carboxamide The title compound was prepared by similar manner to Example 5, starting from the compound of Example 12. Mass: (M+1), 514

EXAMPLE 16

6-(6-Methoxy-7-[3-(5,8-Dioxa-10-azadispiro[2.0.4.3]undecane)propoxy]quinolin-4-yloxy)-N,2-dimethylbenzofuran-3-carboxamide The title compound was prepared by similar manner to Example 6, by use of 6-hydroxy-N,2-dimethylbenzofuran-3-carboxamide instead of 2-methyl-4-fluoro-5-hydroxyindole. Mass: (M+1), 574

EXAMPLE 17

6-(6-Methoxy-7-(3-(7-oxo-5-azaspiro[2.4]heptan-5-yl)propoxy)quinolin-4-yloxy)-N,2-benzofuran-3-carboxamide The title compound was prepared by similar manner to Example 7, starting from the compound of Example 16. Mass: (M+1), 530

EXAMPLE 18

6-(7-(3-(7-Hydroxy-5-azaspiro[2.4]heptan-5-yl)propoxy)-6-methoxyquinolin-4-yloxy)-N,2-dimethylbenzofuran-3-carboxamide The title compound was prepared by similar manner to Example 8, starting from the compound of Example 17. Mass: (M+1), 532

EXAMPLE 19

6-(6-Methoxy-7-(3-(7-methoxy-5-azaspiro[2.4]heptan-5-yl)propoxy)quinolin-4-yloxy)-N,2-dimethylbenzofuran-3-carboxamide The title compound was prepared by similar manner to Example 9, starting from the compound of Example 18. Mass: (M+1), 546

EXAMPLE 20

6-(6-Methoxy-7-(3-(7-methylene-5-azaspiro[2.4]heptan-5-yl)propoxy)quinolin-4-yloxy)-N,2-dimethylbenzofuran-3-carboxamide The title compound was prepared by similar manner to Example 10, starting from the compound of Example 17. Mass: (M+1), 528

EXAMPLE 21

6-(6-Methoxy-7-[2-(5,8-Dioxa-10-azadispiro[2.0.4.3]undecane)ethoxy]quinolin-4-yloxy)-N-methyl-1-naphthamide The title compound was prepared by similar manner to Example 1, by use of 6-hydroxy-N-methyl-1-naphthamide instead of 2-methyl-4-fluoro-5-hydroxyindole in Method A. Mass: (M+1), 556

EXAMPLE 22

6-(6-Methoxy-7-(2-(7-oxo-5-azaspiro[2.4]heptan-5-yl)ethoxy)quinolin-4-yloxy)-N-methyl-1-naphthamide The title compound was prepared by similar manner to Example 2, starting from the compound of Example 21. Mass: (M+1), 512

EXAMPLE 23

6-(7-(2-(7-Hydroxy-5-azaspiro[2.4]heptan-5-yl)ethoxy)-6-methoxyquinolin-4-yloxy)-N-methyl-1-naphthamide The title compound was prepared by similar manner to Example 3, starting from the compound of Example 22. Mass: (M+1), 514

EXAMPLE 24

6-(6-Methoxy-7-(2-(7-methoxy-5-azaspiro[2.4]heptan-5-yl)ethoxy)quinolin-4-yloxy)-N-methyl-1-naphthamide The title compound was prepared by similar manner to Example 4, starting from the compound of Example 23. Mass: (M+1), 528

EXAMPLE 25

6-(6-Methoxy-7-(2-(7-methylene-5-azaspiro[2.4]heptan-5-yl)ethoxy)quinolin-4-yloxy)-N-methyl-1-naphthamide The title compound was prepared by similar manner to Example 5, starting from the compound of Example 22. Mass: (M+1), 510

EXAMPLE 26

6-(6-Methoxy-7-[3-(5,8-Dioxa-10-azadispiro [2.0.4.3]undecane)propoxy]quinolin-4-yloxy)-N-methyl-1-naphthamide The title compound was prepared by similar manner to Example 6, by use of 6-hydroxy-N-methyl-1-naphthamide instead of 2-methyl-4-fluoro-5-hydroxyindole. Mass: (M+1), 570

EXAMPLE 27

6-(6-Methoxy-7-(3-(7-oxo-5-azaspiro[2.4]heptan-5-yl)propoxy)quinolin-4-yloxy)-N-methyl-1-naphthamide The title compound was prepared by similar manner to Example 7, starting from the compound of Example 26. Mass: (M+1), 526

EXAMPLE 28

6-(7-(3-(7-Hydroxy-5-azaspiro[2.4]heptan-5-yl)propoxy)-6-methoxyquinolin-4-yloxy)-N-methyl-1-naphthamide The title compound was prepared by similar manner to Example 8, starting from the compound of Example 27. Mass: (M+1), 528

EXAMPLE 29

6-(6-Methoxy-7-(3-(7-methoxy-5-azaspiro[2.4]heptan-5-yl)propoxy)quinolin-4-yloxy)-N-methyl-1-naphthamide The title compound was prepared by similar manner to Example 9, starting from the compound of Example 28. Mass: (M+1), 542

EXAMPLE 30

6-(6-Methoxy-7-(3-(7-methylene-5-azaspiro[2.4] heptan-5-yl)propoxy)quinolin-4-yloxy)-N-methyl-1-naphthamide The title compound was prepared by similar manner to Example 10, starting from the compound of Example 27. Mass: (M+1), 524

EXAMPLES OF SALT FORMATION

Compound from Example 1 (or Example 2 to Example 30) (100 mg) was dissolved into EtOAc (5 ml) and to the solution was added 2N HCl/Ether solution (0.5 ml). The solution was evaporated to give a solid as its HCl salt.

The other pharmaceutical acceptable salts, such as hydrobromic, sulphufic, nitric, phosphoric acid; or succinic, maleic, acetic, fumaric, citic, tartaric, benzoic, p-toluenesulfonic, methanesulfonic, naphthalenesulfonic acid salt can be prepared in the similar manner. It can be made at higher temperatures with EtOH, MeOH or isopropanol as well as with other pharmaceutical acceptable solvents.

EXAMPLES OF FORMULATION

The following are the examples of the formulations and these are purely illustrative and in no way to be interpreted as restrictive.

FORMULATION EXAMPLE 1

Each capsule contains:

| | |
|---|---:|
| Compound Example 1 | 100.0 mg |
| (or Example 2 to Example 30) | |
| Corn starch | 23.0 mg |
| Calcium carboxymethyl cellulose | 22.5 mg |
| Hydroxypropylmethyl cellulose | 3.0 mg |
| Magnesium stearate | 1.5 mg |
| | 150.0 mg |

FORMULATION EXAMPLE 2

A solution contains:

| | |
|---|---:|
| Compound Example 20 | 1 to 10 g |
| (or Example 2 to Example 30) | |
| Acetic acid or sodium hydroxide | 0.5 to 1 g |
| Ethyl p-hydroxybenzoate | 0.1 g |
| Purified water | 88.9 to 98.4 g |
| | 100.0 g |

FORMULATION EXAMPLE 3

A powder for admixing with feedstuff contains:

| | |
|---|---:|
| Compound Example 20 | 1 to 10 g |
| (or Example 2 to Example 30) | |
| Corn starch | 98.5 to 89.5 g |
| Light anhydrous silicic acid | 0.5 g |
| | 100.0 g |

What is claimed is:

1. A compound of formula I

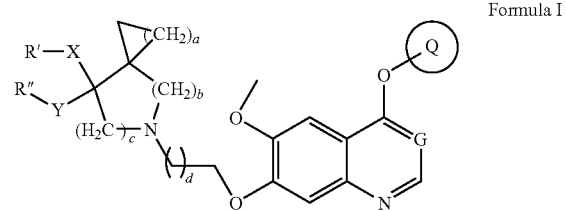

Formula I

Wherein

Ring Q is a bicyclic aryl or a bicyclic heterocyclyl moiety, selected from:

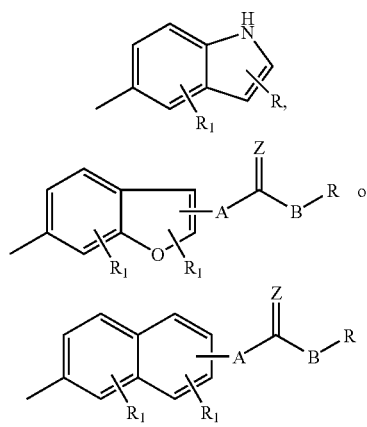

R is each independently selected from H, halogen, halogeno-lower alkyl, lower alkyl, hydroxy, lower alkoxy, lower alkoxyalkoxy, lower alkenyl, lower alkynyl, amino, alkylamino, alkoxyamino, cycloalkyl, cycloalkenyl, aryl or heterocyclyl;

$R_1$ is selected from H, halogen, halogeno-lower alkyl, lower alkyl, hydroxy, lower alkoxy, lower alkoxyalkoxy, lower alkenyl, or lower alkynyl;

A is selected from direct bond of —N(R')—;

B is selected from direct bond, O, —N(R')—, —C(=Z)—, —C(=Z)N(R')—, lower alkylenyl-C(=Z)— or lower alkylenyl-C(=Z)N(R')—;

Z is selected from O or S;

a is selected from 1, 2, 3, 4 or 5;

b, c and d are each independently selected from 1, 2, or 3;

G is selected from C—R, C—(CN) or N;

R' and R" are not presented, when X and Y are selected from (i) X combines Y to be an oxygen or methylene, (ii) X is hydrogen, Y is hydrogen, (iii) X is hydrogen, Y is hydroxy or its optical isomer;

R' and R" are each independently selected from halogeno-lower alkyl, lower alkyl, lower alkoxy, hydroxy, lower alkylhydroxy, when X and Y are selected from (i) X is hydrogen, Y is O, S or its optical isomer, (ii) X and Y are both O or S, or (iii) X is O and Y is S; optionally R' and R" combine to form a 5 to 7 membered ring with X, Y and the said ring can be unsubstituted or substituted independently by up to three substituents, or a pharmaceutically acceptable salt thereof.

2. A compound according to claim 1, wherein

Ring Q is a bicyclic aryl or a bicyclic heterocyclyl moiety, selected from:

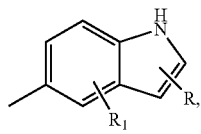

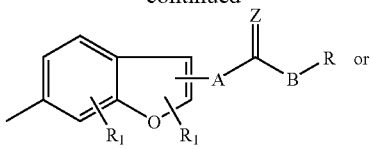

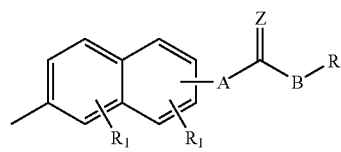

R is each independently selected from H, halogen, halogeno-lower alkyl, lower alkyl, hydroxy, lower alkoxy, lower alkoxyalkoxy, lower alkenyl, lower alkynyl, amino, alkylamino, alkoxyamino, cycloalkyl, cycloalkenyl, aryl or heterocyclyl; preferably selected from H, halogen, halogeno-lower alkyl, lower alkyl;

$R_1$ is selected from H, halogen, halogeno-lower alkyl, lower alkyl, hydroxy, lower alkoxy, lower alkoxyalkoxy, lower alkenyl, or lower alkynyl; preferably selected from H, halogen, halogeno-lower alkyl, lower alkyl;

A is selected from direct bond or —N(R')—; preferably selected from direct bond or —NH—;

B is selected from direct bond, O, —N(R')—, —C(=Z)—, —C(=Z)N(R')—, lower alkylenyl-C(=Z)—or lower; alkylenyl-C(=Z)N(R')—; preferably selected from —NH—, —C(=O)—, or —C(=O)NH—;

Z is selected from O or S; preferably O;

a is selected from 1, 2, 3, 4 or 5; preferably 1, 2 or 3;

b, c and d are each independently selected from 1, 2, or 3; preferably 1 or 2;

G is selected from C—R, C—(CN) or N; preferably C—R or N, more preferably CH;

R' and R" are not presented, when X and Y are selected from (i) X combines Y to be an oxygen or methylene, (ii) X is hydrogen, Y is hydrogen, (iii) X is hydrogen, Y is hydroxy or its optical isomer; the preferred moieties are each independently selected from ketone, methylene or hydroxy or optical isomer of said hydroxy;

R' and R" are each independently selected from halogeno-lower alkyl, lower alkyl, lower alkoxy, hydroxy, lower alkylhydroxy, when X and Y are selected from (i) X is hydrogen, Y is O, S or its optical isomer, (ii) X and Y are both O or S, or (iii) X is O and Y is S; optionally R' and R" combine to form a 5 to 7 membered ring with X, Y and the said ring can be unsubstituted or substituted independently by up to three substituents, the preferred moieties are each independently selected from alkoxy or optical isomers of said alkoxy, cyclic ketal, cyclic thioketal, or cyclic thioxolane which may be unsubstituted or substituted with lower alkyl, aryl or heterocyclyl; or a pharmaceutically acceptable salt thereof.

3. A compound according to claim 1, represented by Formula II
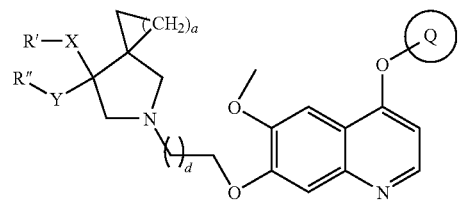
Formula II
Wherein
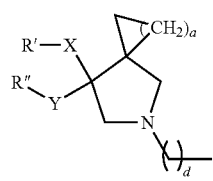
is independently selected from:
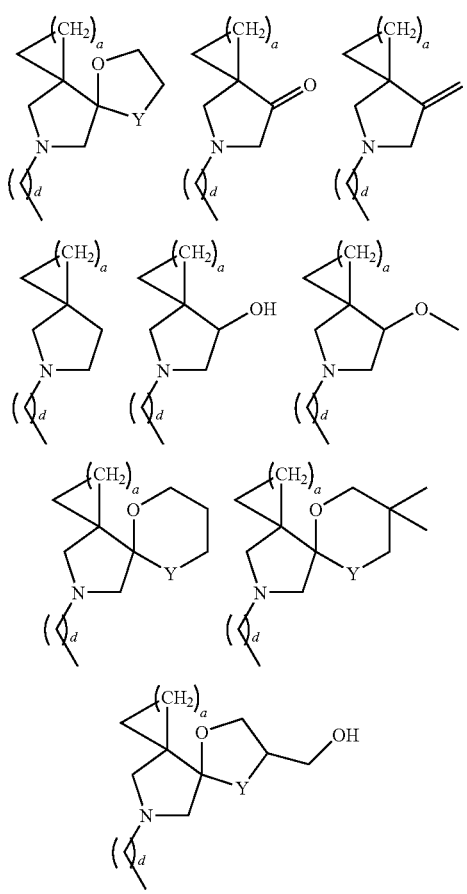
a or d are 1, 2, or 3; Y is O or S
Ring Q is independently selected from
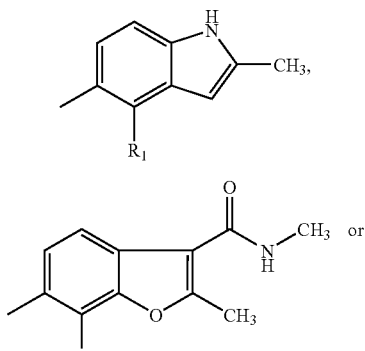
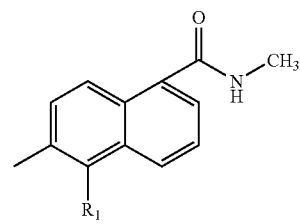
$R_1$ is H or F
or a pharmaceutically acceptable salt thereof.
4. A compound according to claim 1 that is selected from the group consisting of:
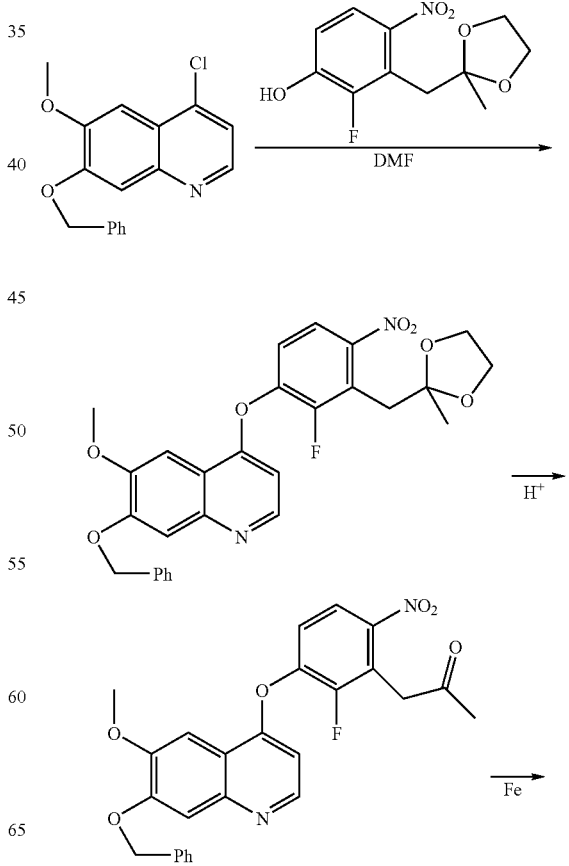

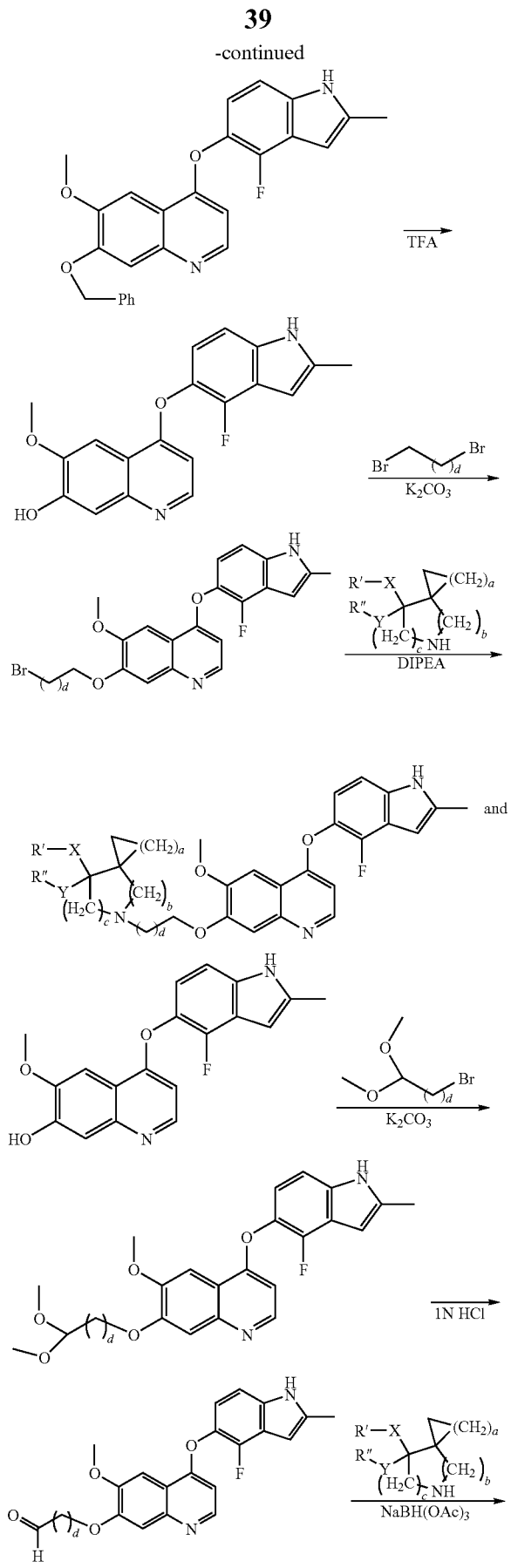

or a pharmaceutically acceptable salt thereof.

5. A compound according to claim 1 that is selected from the group consisting of:

4-(4-Fluoro-2-methyl-1H-indol-5-yloxy)-6-methoxy-7-[2-(5,8-Dioxa-10-azadispiro[2.0.4.3]-undecane)ethoxy]quinoline 5-(2-(4-(4-Fluoro-2-methyl-1H-indol-5-yloxy)-6-methoxyquinolin-7-yloxy)ethyl)-5-azaspiro[2.4]-heptan-7-one 5-(2-(4-(4-fluoro-2-methyl-1H-indol-5-yloxy)-6-methoxyquinolin-7-yloxy)ethyl)-5-azaspiro[2.4]-heptan-7-ol 4-(4-Fluoro-2-methyl-1H-indol-5-yloxy)-6-methoxy-7-(2-(7-methoxy-5-azaspiro[2.4]heptan-5-yl)ethoxy)quinoline 4-(4-Fluoro-2-methyl-1H-indol-5-yloxy)-6-methoxy-7-(2-(7-methylene-5-azaspiro[2.4]heptan-5-yl)ethoxy)quinoline 4-(4-fluoro-2-methyl-1H-indol-5-yloxy)-6-methoxy-7-[3-(5,8-Dioxa-10-azadispiro[2.0.4.3]-undecane)propoxy]quinoline 5-(3-(4-(4-Fluoro-2-methyl-1H-indol-5-yloxy)-6-methoxyquinolin-7-yloxy)propyl)-5-azaspiro[2.4]-heptan-7-one 5-(3-(4-(4-Fluoro-2-methyl-1H-indol-5-yloxy)-6-methoxyquinolin-7-yloxy)propyl)-5-azaspiro[2.4]-heptan-7-ol 4-(4-Fluoro-2-methyl-1H-indol-5-yloxy)-6-methoxy-7-(3-(7-methoxy-5-azaspiro[2.4]heptan-5-yl)propoxy)quinoline 4-(4-Fluoro-2-methyl-1H-indol-5-yloxy)-6-methoxy-7-(3-(7-methylene-5-azaspiro[2.4]heptan-5-yl)propoxy)quinoline 6-(6-Methoxy-7-[2-(5,8-Dioxa-10-azadispiro[2.0.4.3]undecane)ethoxy]quinolin-4-yloxy)-N,2-dimethylbenzofuran-3-carboxamide 6-(6-Methoxy-7-(2-(7-oxo-5-azaspiro[2.4]heptan -5-yl)ethoxy)quinolin-4-yloxy)-N,2-dimethylbenzofuran-3-carboxamide 6-(7-(2-(7-Hydroxy-5-azaspiro[2.4]heptan-5-yl)ethoxy)-6-methoxyquinolin-4-yloxy)-N,2-dimethylbenzofuran-3-carboxamide 6-(6-Methoxy-7-(2-(7-methoxy-5-azaspiro[2.4]heptan-5-yl)ethoxy)quinolin-4-yloxy)-N,2-dimethylbenzofuran-3-carboxamide 6-(6-Methoxy-7-(2-(7-methylene-5-azaspiro[2.4]heptan-5-yl)ethoxy)quinolin-4-yloxy)-N,2-dimethyl-benzofuran-3-carboxamide 6-(6-Methoxy-7-[3-(5,8-Dioxa-10-azadispiro[2.0.4.3]undecane)propoxy]quinolin-4-yloxy)-N,2-dimethylbenzofuran-3-carboxamide 6-(6-Methoxy-7-(3-(7-oxo-5-azaspiro[2.4]heptan -5-yl)propoxy)quinolin-4-yloxy)-N,2-dimethyl-benzofuran-3-carboxamide 6-(7-(3-(7-Hydroxy-5-azaspiro[2.4]heptan-5-yl)propoxy)-6-methoxyquinolin-4-yloxy)-N,2-dimethyl-benzofuran-3-carboxamide 6-(6-Methoxy-7-(3-(7-methoxy-5-azaspiro[2.4]heptan-5-yl)propoxy)quinolin-4-yloxy)-N,2-dimethyl-benzofuran-3-carboxamide 6-(6-Methoxy-7-(3-(7-methylene-5-azaspiro[2.4]heptan-5-yl)propoxy)quinolin-4-yloxy)-N,2-dimethylbenzofuran-3-carboxamide 6-(6-Methoxy-7-[2-(5,8-Dioxa-10-azadispiro[2.0.4.3]undecane)ethoxy]quinolin-4-yloxy)-N-methyl-1-naphthamide 6-(6-Methoxy-7-(2-(7-oxo-5-azaspiro[2.4]heptan -5-yl)ethoxy)quinolin-4-yloxy)-N-methyl-1-naphthamide 6-(7-(2-(7-Hydroxy-5-azaspiro[2.4]heptan-5-yl)ethoxy)-6-methoxyquinolin-4-yloxy)-N-methyl-1-naphthamide 6-(6-Methoxy-7-(2-(7-methoxy-5-azaspiro[2.4]heptan-5-yl)ethoxy)quinolin-4-yloxy)-N-methyl-1-naphthamide 6-(6-Methoxy-7-(2-(7-methylene-5-azaspiro[2.4]heptan-5-yl)ethoxy)quinolin-4-yloxy)-N-methyl-1-naphthamide 6-(6-Methoxy-7-[3-(5,8-Dioxa-10-azadispiro[2.0.4.3]undecane)propoxy]quinolin-4-yloxy)-N-methyl-1-naphthamide 6-(6-Methoxy-7-(3-(7-oxo-5-azaspiro[2.4]heptan -5-yl)propoxy)quinolin-4-yloxy)-N-methyl-1-naphthamide 6-(7-(3-(7-Hydroxy-5-azaspiro[2.4]heptan-5-yl)propoxy)-6-methoxyquinolin-4-yloxy)-N-methyl-1-naphthamide 6-(6-Methoxy-7-(3-(7-methoxy-5-azaspiro[2.4]heptan-5-yl)propoxy)quinolin-4-yloxy)-N-methyl-1-naphthamide 6-(6-Methoxy-7-(3-(7-methylene-5-azaspiro[2.4]heptan-5-yl)propoxy)quinolin-4-yloxy)-N-methyl-1-naphthamide or a pharmaceutically acceptable salt selected from hydrochloric, hydrobromic, sulphuric, nitric, phosphoric acid; or succinic, maleic, acetic, fumaric, citic, tartaric, benzoic, p-toluenesulfonic, methanesulfonic or naphthalenesulfonic acid salt.

6. A method of producing a compound having the formula I of claim 1, representing by use of following chemistry process:

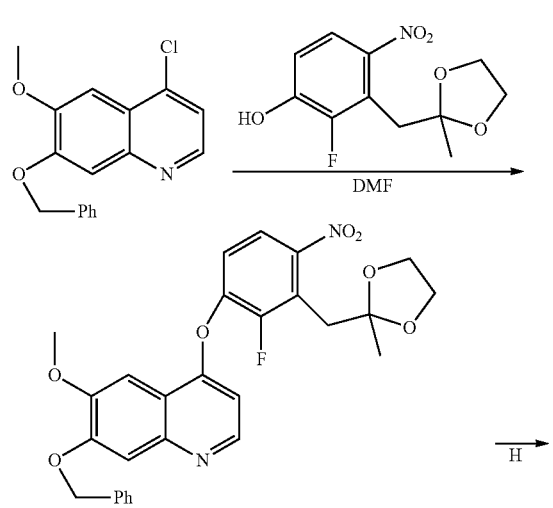

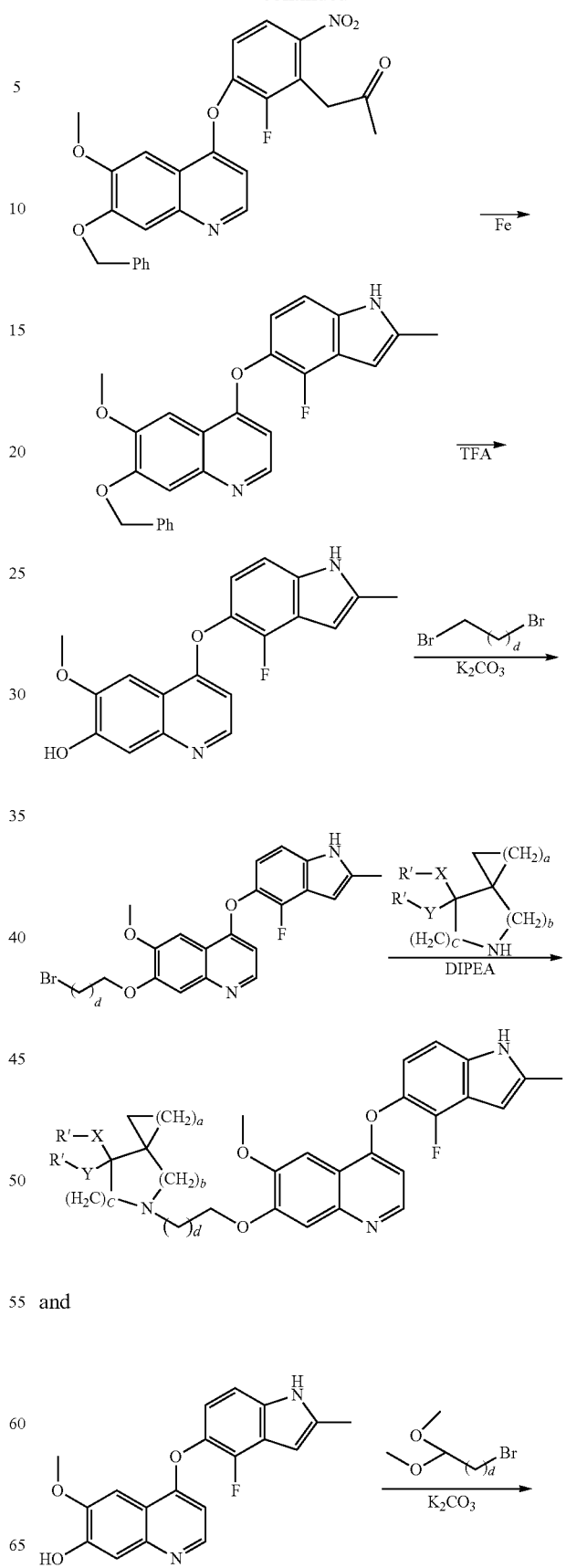

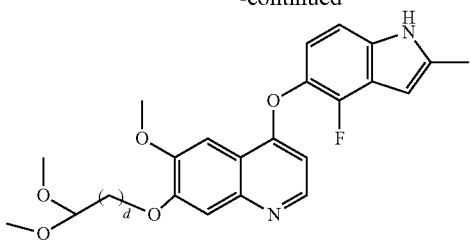

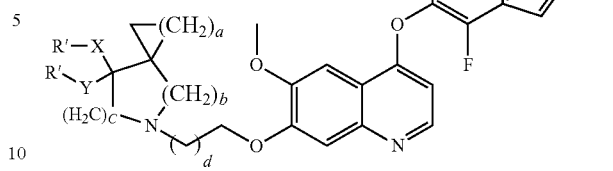

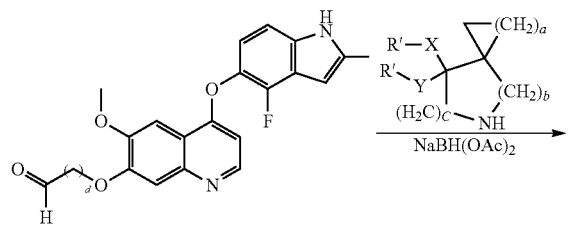

7. A pharmaceutical composition that comprises as an active ingredient a compound as defined in any one of claims 1-5 or a pharmaceutically acceptable salt of the compound, or a hydrate or solvate of the compound and a pharmaceutically acceptable carrier.

8. A method of treating cancer in a subject in need thereof by administering an effective amount of a compound as in any of claim 1-5.

9. A method of treating cancer in a subject in need thereof by administering an effective amount of a compound as in any of claim 1-5.

* * * * *